(12) United States Patent
Liu et al.

(10) Patent No.: US 7,957,001 B2
(45) Date of Patent: Jun. 7, 2011

(54) WAVELENGTH-MODULATION SPECTROSCOPY METHOD AND APPARATUS

(75) Inventors: Xiaoyong Liu, Malden, MA (US); John McKinley Poole, Maynard, MA (US); Yufeng Huang, North Chelmsford, MA (US); Daniel M. Stearns, Canton, MA (US); Michael J. Gambuzza, Pepperell, MA (US); Gene Smith Berkowitz, Sudbury, MA (US); Anthony Kowal, Berlin, MA (US); Hejie Li, Schenectady, NY (US); Shawn D. Wehe, Niskayuna, NY (US)

(73) Assignee: GE Infrastructure Sensing, Inc., Billerica, MA (US)

( * ) Notice: Subject to any disclaimer, the term of this patent is extended or adjusted under 35 U.S.C. 154(b) by 294 days.

(21) Appl. No.: 12/249,156

(22) Filed: Oct. 10, 2008

(65) Prior Publication Data

US 2010/0091278 A1 Apr. 15, 2010

(51) Int. Cl.
*G01N 21/31* (2006.01)
(52) U.S. Cl. ........................................ 356/435; 250/345
(58) Field of Classification Search .......... 356/432–435, 356/437, 319; 250/343, 345
See application file for complete search history.

(56) References Cited

U.S. PATENT DOCUMENTS

| | | | |
|---|---|---|---|
| 3,893,771 A | 7/1975 | Bell | |
| 4,068,125 A | 1/1978 | Bell | |
| 4,953,390 A | 9/1990 | Krempl et al. | |
| 5,107,118 A | 4/1992 | Murray, Jr. et al. | |
| 5,134,276 A | 7/1992 | Hobbs | |
| 5,173,749 A | 12/1992 | Tell et al. | |
| 5,317,156 A | 5/1994 | Cooper et al. | |
| 5,448,071 A | 9/1995 | McCaul et al. | |
| 5,491,341 A | 2/1996 | McCaul et al. | |
| 5,528,040 A | 6/1996 | Lehmann | |

(Continued)

FOREIGN PATENT DOCUMENTS

EP    1544604 A1    6/2005

(Continued)

OTHER PUBLICATIONS

Thomas L. Markey, Park Evaluations & Translations, 850 Seventh Ave. 5th Floor, New York, N.Y. 10019, pp. 1-19.

(Continued)

*Primary Examiner* — L. G Lauchman
(74) *Attorney, Agent, or Firm* — Global Patent Operation; Mark A. Conklin

(57) ABSTRACT

In one embodiment of the spectroscopy method, the method comprises the steps of modulating the wavelength of a monochromatic radiation at a modulation amplitude and a modulation frequency; determining a first variable representative of an absorbance of an analyte in a sample; and demodulating by phase-sensitive detection the first variable at a harmonic of the modulation frequency to produce a harmonic spectrum of the analyte. In one embodiment of the spectroscopy apparatus, the apparatus comprises a laser diode integrated with a first photodetector configured to detect an intensity of a backward emission from the laser diode and act as a reference detector; a second photodetector configured to detect an intensity of laser radiation exiting a sample; and electronic circuitry coupled to the laser diode and the photodetectors, configured to acquire and process spectra of the sample. In another embodiment, the spectroscopy apparatus comprises a beam splitter configured to split the laser radiation into a first radiation portion and a second radiation portion and a first photodetector configured to detect the intensity of the first radiation portion.

11 Claims, 4 Drawing Sheets

U.S. PATENT DOCUMENTS

| | | | |
|---|---|---|---|
| 5,550,636 | A | 8/1996 | Hagans et al. |
| 5,572,031 | A | 11/1996 | Cooper et al. |
| 5,625,189 | A | 4/1997 | McCaul et al. |
| 5,636,035 | A | 6/1997 | Whittaker et al. |
| 5,640,245 | A | 6/1997 | Zybin et al. |
| 5,742,054 | A | 4/1998 | Atkinson |
| 5,742,200 | A | 4/1998 | He |
| 5,742,399 | A | 4/1998 | McAndrew et al. |
| 5,818,578 | A | 10/1998 | Inman et al. |
| 5,835,230 | A | 11/1998 | McAndrew et al. |
| 5,847,392 | A | 12/1998 | Van Den Berg et al. |
| 5,880,850 | A | 3/1999 | McAndrew et al. |
| 5,949,537 | A | 9/1999 | Inman et al. |
| 5,963,336 | A | 10/1999 | McAndrew et al. |
| 5,969,825 | A | 10/1999 | Bomse et al. |
| 6,040,914 | A * | 3/2000 | Bortz et al. .................. 356/435 |
| 6,064,488 | A | 5/2000 | Brand et al. |
| 6,084,668 | A | 7/2000 | McAndrew et al. |
| 6,150,661 | A | 11/2000 | McCaul et al. |
| 6,154,284 | A | 11/2000 | McAndrew et al. |
| 6,188,475 | B1 | 2/2001 | Inman et al. |
| 6,292,756 | B1 | 9/2001 | Lievois et al. |
| 6,341,521 | B1 | 1/2002 | Bartolomey et al. |
| 6,356,350 | B1 | 3/2002 | Silver et al. |
| 6,420,695 | B1 | 7/2002 | Grasdepot et al. |
| 6,442,736 | B1 | 8/2002 | Girard et al. |
| 6,493,086 | B1 | 12/2002 | McAndrew et al. |
| 6,603,555 | B1 | 8/2003 | Nanami et al. |
| 6,611,335 | B1 | 8/2003 | Hovde |
| 6,639,678 | B1 | 10/2003 | Veale |
| 6,657,198 | B1 | 12/2003 | May |
| 6,741,348 | B2 | 5/2004 | Larsen et al. |
| 6,795,190 | B1 | 9/2004 | Paul et al. |
| 6,876,450 | B2 | 4/2005 | Nanami et al. |
| 7,009,170 | B2 | 3/2006 | Dobbs et al. |
| 7,075,362 | B2 | 7/2006 | North |
| 7,102,751 | B2 | 9/2006 | Harper |
| 7,132,661 | B2 | 11/2006 | May |
| 7,180,595 | B2 | 2/2007 | Willing et al. |
| 7,183,553 | B1 | 2/2007 | Willing et al. |
| 7,262,844 | B2 | 8/2007 | Larsen et al. |
| 7,339,168 | B2 | 3/2008 | May |
| 7,499,169 | B2 * | 3/2009 | Hurvitz et al. ................ 356/432 |
| 7,728,978 | B2 * | 6/2010 | Zhou et al. .................... 356/437 |
| 2003/0218750 | A1 | 11/2003 | Friberg |
| 2005/0030540 | A1 | 2/2005 | Thornton |
| 2005/0286054 | A1 | 12/2005 | Chen et al. |
| 2006/0044562 | A1 | 3/2006 | Hagene et al. |
| 2006/0065834 | A1 | 3/2006 | Flanders et al. |
| 2006/0187976 | A1 | 8/2006 | Mori et al. |
| 2007/0246653 | A1 | 10/2007 | Zhou |
| 2007/0295908 | A1 | 12/2007 | Wilkins et al. |

FOREIGN PATENT DOCUMENTS

| | | |
|---|---|---|
| JP | 60117695 A | 6/1985 |

OTHER PUBLICATIONS

J. Reid and D. Labrie, Second-Harmonic Detection with Tunable Diode Lasers—Comparison of Experiment and Theory, Departments of Engineering Physics and Physics, McMaster University, Hamilton, Ontario, Canada L8S 4M1, pp. 203-210.

Joel A. Silver, Frequency-Modulation Spectroscopy For Trace Species Detection: Theory And Comparison Among Experimental Methods, Applied Optics, Feb. 20, 1992, vol. 31, No. 6, pp. 707-717.

William J. Kessler, Mark G. Allen, Steven J. Davis, Phillip A. Mulhall and Jan A. Polex, Near-IR Diode Laser-Based Sensor for PPB-Level Water Vapor in Industrial Gases, Physical Sciences Inc., 20 New England Business Center, Andover, MA 01810, 1998 Photonics, East, SPIE International, SPIE Paper No. 3537-A30, pp. 1-12.

Mark E. Paige, Commercial Gas Sensing With Vertical Cavity Lasers, Southwest Sciences, Inc., 1570 Pacheco St. Suite E-11, Santa Fe NM 87505, pp. 141-143.

A.R. W. McKellar, The Spectrum of Gaseous Methane at 77 K in the 1.1—2.6 µregion: a benchmark for planetary astronomy[1], *Herzberg Institute of Astrophysics, National Research Council of Canada*, Ottawa, Ont.. Canada K1A 0R6. Received May 10, 1989, pp. 1027-1035.

K. Strong, F. W. Taylor, S. B. Calcutt, J. J. Remedios and J. Ballards, Spectral Parameters of Self-And Hydrogen-Broadened Methane From 2000 to 9500 $cm^{-1}$ For Remote Sounding Of The Atmosphere Of Jupiter, Clarendon Laboratory, University of Oxford, Parks Road, Oxford and §S.E.R.C. Rutherford Appleton Laboratory, Chilton, Didcot, Oxfordshire, U.K.. pp. 363-429.

Shih-Yi Chang and Tai-Ly Tso, Measurement of the Taiwan Ambient Trace Gas Concentration by Kilometer-Pathlength Fourier-Transform Infrared Spectroscopy, Analytical Science, Feb. 1994, vol. 10, Department of Chemistry, National Tsing Hua University, Hsinchu, 30043, Taiwan, R.O.C,, pp. 193-201.

Randy D. May, Computer Processing Of Tunable Diode Laser Spectra, Jet Propulsion Laboratory, California Institute of Technology. 4800 Oak Grove Drive, Pasadena, California 91109, vol. 43, No. 5, 1989, pp. 834-839.

Randy D. May and Christopher R. Webster, Data Processing And Calibration For Tunable Diode Laser Harmonic Absorption Spectrometers, Jet Propulsion Laboratory, California Institute of Technology, 4800 Oak Grove Drive, Pasadena, California 91109, vol. 49. No. 4, 1993, pp. 335-347.

Randy D. May, Open-Path, Near-Infrared Tunable Diode Laser Spectrometer For Atmospheric Measurements of $H_2O$, Jet Propulsion Laboratory, California Institute of Technology, 4800 Oak Grove Drive, Pasadena, California 91109, May 1998, pp. 1-25.

David C. Scott, Robert L. Herman, Christopher R. Webster, Randy D. May, Gregory J. Flesch, and Elisabeth J. Moyer, Airborne Laser Infrared Absorption Spectrometer (ALIAS-II) for In Situ Atmospheric Measurements of $N_2O$, $CH_4$, CO, HCI, and $NO_2$ From Balloon Or Remotely Piloted Aircraft Platforms, Applied Optics, vol. 38, No. 21, Jul. 20, 1999, pp. 4609-4622.

Randy D. May, Next-Generation Diode Laser Gas Sensors For Environmental And Industrial Monitoring, SpectraSensors, Inc., 2400 Lincoln Avenue, Altadena, CA 91001, SPIE—Part of SPIE Conference On Advanced Materials and Optical Systems For Chemical and Biological Detection, Boston MA 1999, vol. 3858, pp. 110-118.

L.S. Rothman et al. The *Hitran* 2004 Molecular Spectroscopic Database, Journal of Quantitative Spectroscopy & Radiative Transfer 96 (2005), pp. 139-204.

PCT/US2009/057228, Search Report and Written Opinion, Sep. 17, 2009.

Zybin A V et al., "Dynamic range improvement and background correction in diode laser atomic absorption spectrometry" Spectrochimica Acta Part B; vol. 54. No. 3-4, Apr. 4, 1999, pp. 613-619, XP002560637, the whole document.

Hejie et al., "Extension of wave length-modulation spectroscopy to large modulation depth for diode laser absorption measurements in high-pressure gasses" APPL. OPT., vol. 45, No. 5. Feb. 10, 2006, pp. 1052-1061, XP002560638, the whole document.

* cited by examiner

WAVELENGTH-MODULATION SPECTROSCOPY METHOD AND APPARATUS

BACKGROUND OF THE INVENTION

The invention relates generally to spectroscopy, and particularly to a wavelength-modulation spectroscopy method and apparatus.

In recent years, wavelength-modulation spectroscopy has become the mainstream technology of laser-based gas analyzers. In wavelength-modulation spectroscopy, a laser is wavelength-modulated at a certain frequency, 1f, passes through a sample, and the transmission coefficient of the sample is demodulated by phase-sensitive detection at a certain harmonic of modulation frequency, to produce a harmonic spectrum. Predominantly, the second harmonic, 2f, is chosen for demodulation frequency. Phase-sensitive detection is an effective noise reduction technique and has made wavelength-modulation spectroscopy a highly sensitive method. The harmonic spectral signal magnitude reflects the concentration of an absorbing analyte in the sample. Specifically for 2f, the peak height of a 2f spectrum is linear with the analyte concentration within a certain range. Such linearity is the foundation of present 2f gas analyzes.

Wavelength-modulation spectroscopy traditionally is transmission-based, i.e., a harmonic spectrum is generated by demodulating the transmission coefficient of the sample. Because it is transmission-based, the harmonic spectral signal magnitude is inherently nonlinear with the analyte concentration, and can be considered linear with the analyte concentration only when the concentration is so low that absorbance is less than 0.05. Consequently, a gas analyzer utilizing wavelength-modulation spectroscopy has a narrow dynamic range, typically less than two decades ($10^2$). Beyond the dynamic range, the harmonic spectral signal magnitude is nonlinear with the analyte concentration. To compensate for such nonlinearity requires a calibration process that is laborious.

In addition, a tunable diode laser wavelength-modulation spectroscopy gas analyzer involves not only laser wavelength modulation but also laser intensity modulation, which asymmetrizes and complicates the resulting harmonic spectrum and makes it difficult to interpret. Therefore, there exists a need for a wavelength-modulation spectroscopy method and apparatus that can overcome these problems and disadvantages.

BRIEF DESCRIPTION OF THE INVENTION

In one embodiment of the spectroscopy method, the method comprises the steps of modulating the wavelength of a monochromatic radiation at a modulation amplitude and a modulation frequency; determining a first variable representative of an absorbance of an analyte in a sample; and demodulating by phase-sensitive detection the first variable at a harmonic of the modulation frequency to produce a harmonic spectrum of the analyte.

In one embodiment of the spectroscopy apparatus, the apparatus comprises a laser diode integrated with a first photodetector configured to detect an intensity of a backward emission from the laser diode and act as a reference detector; a second photodetector configured to detect an intensity of laser radiation exiting a sample; and electronic circuitry coupled to the laser diode and the photodetectors, configured to acquire and process spectra of the sample. In another embodiment, the spectroscopy apparatus comprises a beam splitter configured to split the laser radiation into a first radiation portion and a second radiation portion and a first photodetector configured to detect the intensity of the first radiation portion.

BRIEF DESCRIPTION OF THE DRAWINGS

The drawings are not necessarily to scale, emphasis instead generally being placed upon illustrating the principles of the invention. In the drawings, like numerals are used to indicate like parts throughout the various views.

DETAILED DESCRIPTION OF THE INVENTION

Figure 1:
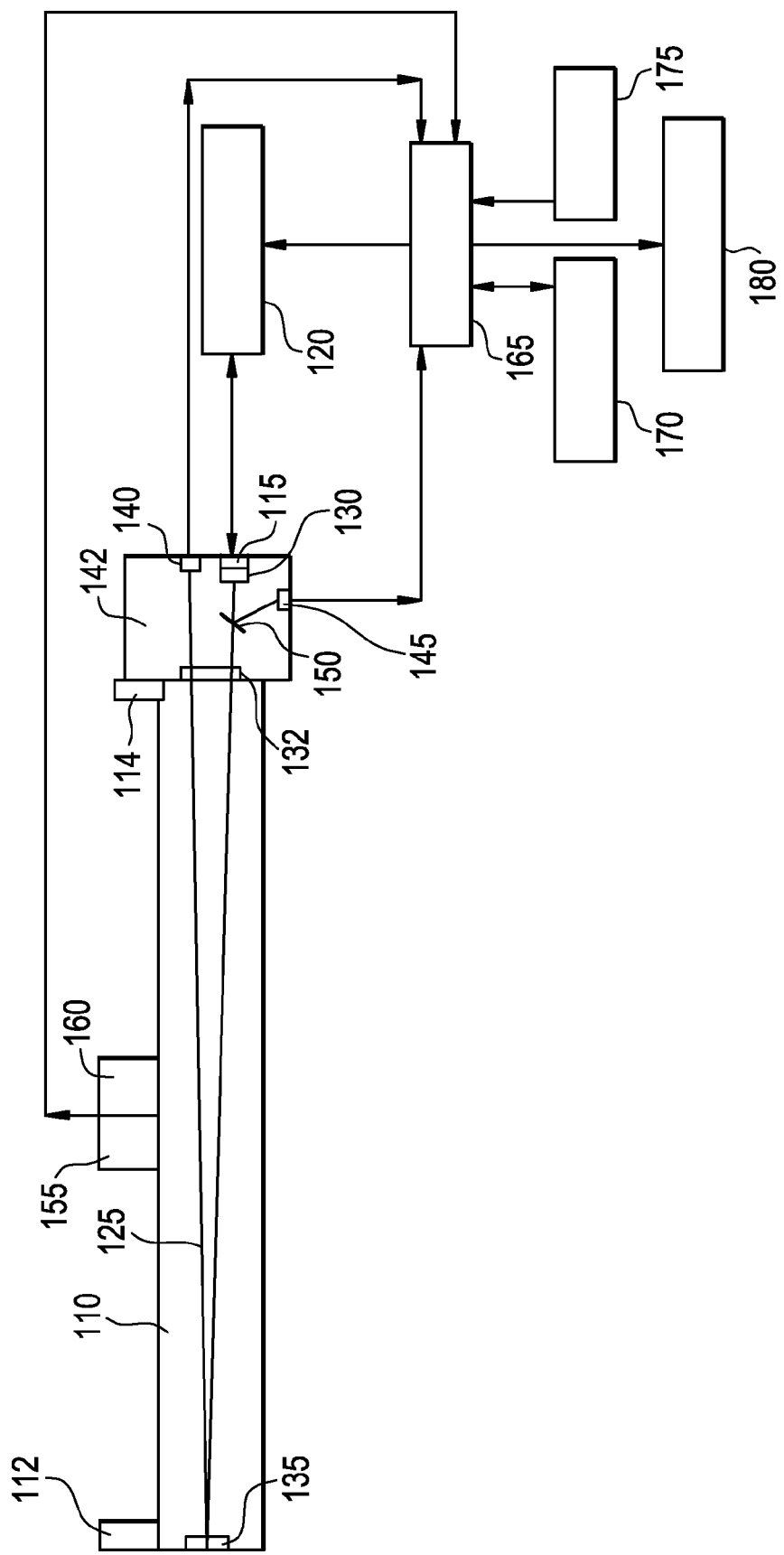
FIG. 1 illustrates a component diagram of a wavelength-modulation spectroscopy apparatus in one embodiment of the invention.

In one embodiment of the invention, there is provided a wavelength-modulation spectroscopy apparatus, a component diagram of which is illustrated in FIG. 1. The apparatus can comprise a monochromatic radiation emitting device 115, which in one embodiment can be provided by a laser emitting device. The apparatus can further comprise, a collimator 130 that collimates the monochromatic radiation 125, a window 132 that transmits the monochromatic radiation 125 but blocks analyte from entering the chamber 142, an absorption cell 110 that contains and conducts a sample via a sample inlet 112 and a sample outlet 114, a mirror 135 at the end of absorption cell 110 that can reflect at least a portion of the monochromatic radiation 125 back to the chamber 142 through the window 132, and a photodetector 140 that can detect the intensity of monochromatic radiation 125 exiting the absorption cell 110.

In one embodiment of the invention, the monochromatic radiation emitting device 115 can be provided by a laser diode. The laser diode can be integrated with a thermoelectric cooler (TEC), a temperature sensor, and a photodetector that can detect the intensity of backward emission from the laser diode. For a particular laser diode, the ratio of the intensity of main laser beam and that of backward emission is constant. Therefore, the intensity of backward emission can be representative of the intensity of light entering the sample, and can be used as a reference for certain spectroscopy applications.

There are several advantages of using a built-in photodetector as a reference detector, including the cost-effectiveness, simplified system design, and improved manufacturability and stability of the resulting system.

In another embodiment of the invention, an external reference photodetector 145 can be employed in addition to, or instead of, the built-in photodetector. As illustrated in FIG. 1, a beam splitter 150 can be configured to split the monochromatic radiation beam 125. A portion of the monochromatic radiation 125 can be detected by a reference photodetector 145 that is separate from the monochromatic radiation emitting device 115, while another portion of the monochromatic radiation 125 can enter the absorption cell 110. The beam splitter 150 can be provided by an uncoated glass plate or wedge, which in one embodiment can reflect about 5% of incident monochromatic radiation intensity and can transmit about 90% of incident monochromatic radiation intensity. The intensity of the monochromatic radiation 125 detected by the reference photodetector 145 can be representative of the intensity of the monochromatic radiation 125 entering the sample. This configuration can be suitable, e.g., for spectroscopy applications where a monochromatic radiation emitting device 115 with a built-in photodetector is not readily available for a desired monochromatic radiation wavelength, where an external reference photodetector 145 is preferred, or where it is necessary to monitor the concentration of the analyte leaking into the chamber 142 to ensure the data integrity. The absorption path length between a laser diode and a built-in photodetector can be too limited, e.g., about 1 mm, to produce a meaningful spectrum of the analyte that might have entered the laser chamber 142, unless the analyte concentration is relatively high. The relatively large distance between the monochromatic radiation emitting device 115 and the external reference detector 145 can enable the detection of possible leaks of the analyte into the chamber 142.

In one embodiment, the apparatus can comprise electronic circuitry 165, which can be configured to generate a drive waveform to drive the laser diode and control laser temperature through a driving circuit 120; to pre-amplify, acquire, and process photodetectors signals to generate a spectrum; when required, to acquire sample pressure and temperature information from a pressure sensor 155 and a temperature sensor 160 measuring sample pressure and temperature, respectively; and when required, to determine analyte concentration from the measured spectrum, pressure and temperature of the sample. In one embodiment, the apparatus can further comprise a display 180, a keypad 175, and one or more I/O interfaces 170.

The apparatus can be configured to perform direct absorption or harmonic spectroscopy measurement. The advantages of having a reference detector, as opposed to a single photodetector apparatus, include the cancellation of common-mode noise, and elimination of the need to approximate the incident monochromatic radiation intensity that may adversely affect the accuracy. The apparatus does not necessarily require balancing the measurement and reference channels and thus can use a less-expensive beam splitter 150, such as a regular glass plate or wedge, or more conveniently when the monochromatic radiation is provided by a laser diode, take the backward emission from the laser diode as reference.

In another embodiment of the invention, there is provided an absorbance-based wavelength-modulation spectroscopy method in which a phase-sensitive demodulation can be performed on the absorbance of a sample.

In spectroscopy, absorbance A is defined as:

$$A(\nu) = \ln\frac{I_0(\nu)}{I(\nu)} = \ln\frac{1}{\tau(\nu)} \quad (1)$$

where $I_0(\nu)$ and $I(\nu)$ are the intensities of monochromatic radiation at a frequency $\nu$ entering and exiting a sample, respectively, and transmission coefficient $$\tau(\nu) = \frac{I(\nu)}{I_0(\nu)}.$$

The Beer-Lambert law provides:

$$A(\nu) = XPS(T)L\Phi(\nu) \quad (2)$$

where X is the concentration of absorbing analyte expressed as the mole fraction of analyte in the sample, P is the total pressure of sample, S(T) is the spectral line intensity which is temperature-dependent, L is the absorption path length, and $\Phi(\nu)$ is the spectral line profile function.

Assuming that a monochromatic radiation, such as a laser, is wavelength-modulated at a frequency $f$, its electromagnetic frequency is $$\nu(t) = \bar{\nu}(t) + \alpha\cos(\omega t) \quad (3)$$

where $\bar{\nu}(t)$ is the center frequency of the monochromatic radiation, $\alpha$ is the wavelength modulation amplitude, and $\omega$ is the angular frequency relating to the wavelength modulation frequency $f$ by $\omega = 2\pi f$.

In one embodiment of the invention, both intensities $I_0(\nu)$ and $I(\nu)$ can be measured, and the absorbance $A(\nu)$, instead of transmission coefficient $\tau(\nu)$, can be demodulated, taking advantage of the apparent linearity of absorbance relative to the analyte concentration provided by the Beer-Lambert law. According to the Beer-Lambert law, the $n^{th}$ harmonic spectral signal magnitude can be expressed as follows:

$$H_n(\bar{\nu}, a) = \frac{1}{\pi}\int_{-\pi}^{\pi}\ln\frac{I_0(\bar{\nu}(t) + a\cos(\omega t))}{I(\bar{\nu}(t) + a\cos(\omega t))}\cos(n\omega t)\,d(\omega t) \quad (4)$$

$$= \frac{1}{\pi}\int_{-\pi}^{\pi}A(\bar{\nu}(t) + a\cos(\omega t))\cos(n\omega t)\,d(\omega t)$$

$$= \frac{XPS(T)L}{\pi}\int_{-\pi}^{\pi}\Phi(\bar{\nu}(t) + a\cos(\omega t))\cos(n\omega t)\,d(\omega t)$$

The second harmonic 2f is a special case of equation (4), corresponding to n=2.

Figure 2:
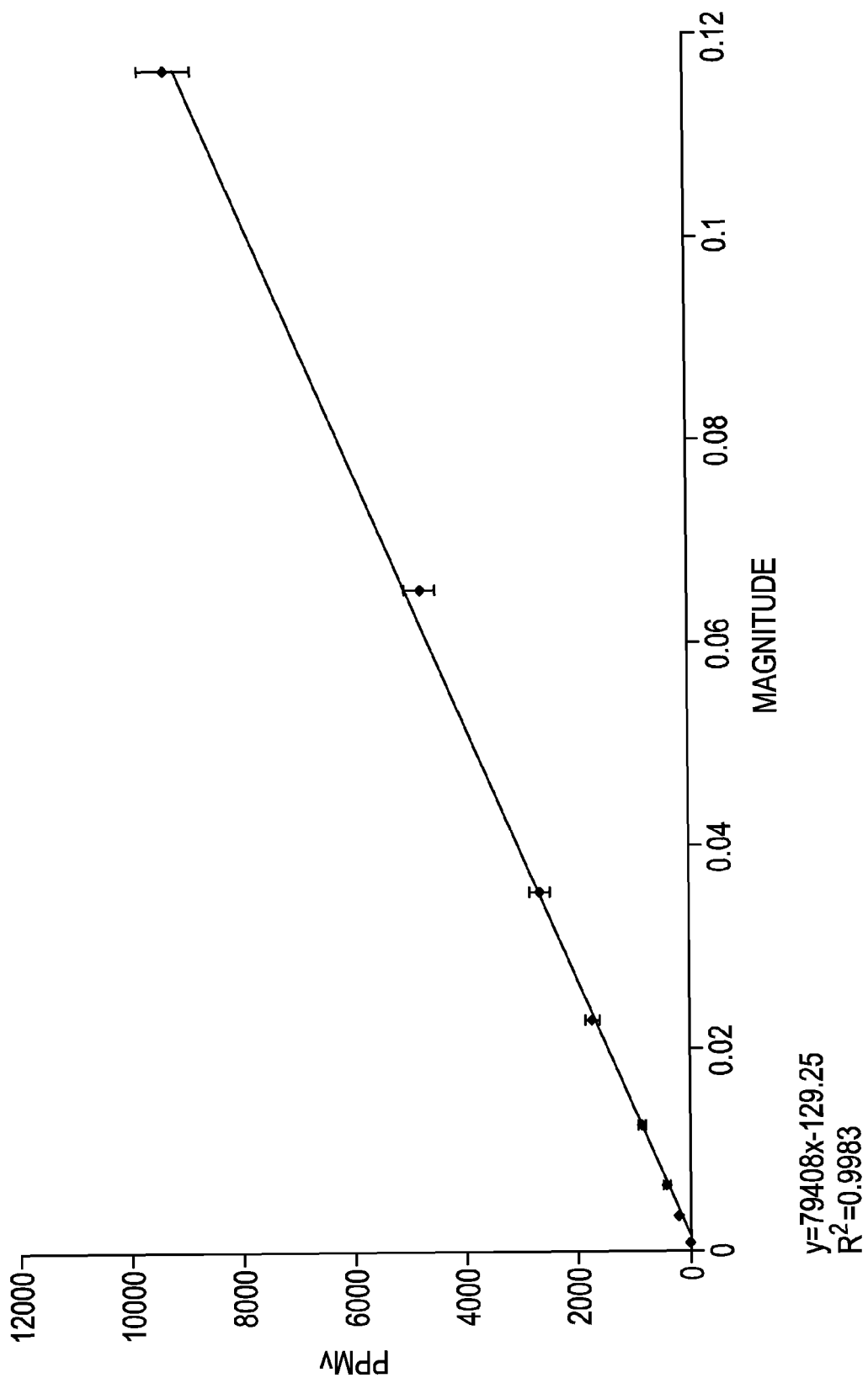
FIG. 2 illustrates an example of the dynamic range of an absorbance-based wavelength-modulation spectroscopy hygrometer in one embodiment of the invention.

By making wavelength-modulation spectroscopy absorbance-based, the signal magnitude of resulting spectrum can become linear relative to the analyte concentration. As a result, the dynamic range of an absorbance-based wavelength-modulation spectroscopy apparatus according to the invention can be limited only by the apparatus sensitivity. In practice, the dynamic range of an absorbance-based wavelength-modulation spectroscopy apparatus according to the invention can cover more than three decades ($10^3$) of analyte concentration. This is a dramatic improvement over a transmission-based wavelength-modulation spectroscopy apparatus. FIG. 2 illustrates an example of the broad dynamic range of an absorbance-based wavelength-modulation spectroscopy hygrometer according to one embodiment of the invention. In the graph of FIG. 2, the abscissa axis represents a unitless absorbance-based 2f signal magnitude, and the ordinates axis represents the corresponding moisture content in ppmV. Full-range linearity provided by the absorbance-based wavelength-modulation spectroscopy method of the invention can be especially beneficial, e.g., for industry gas analysis.

Figure 3:
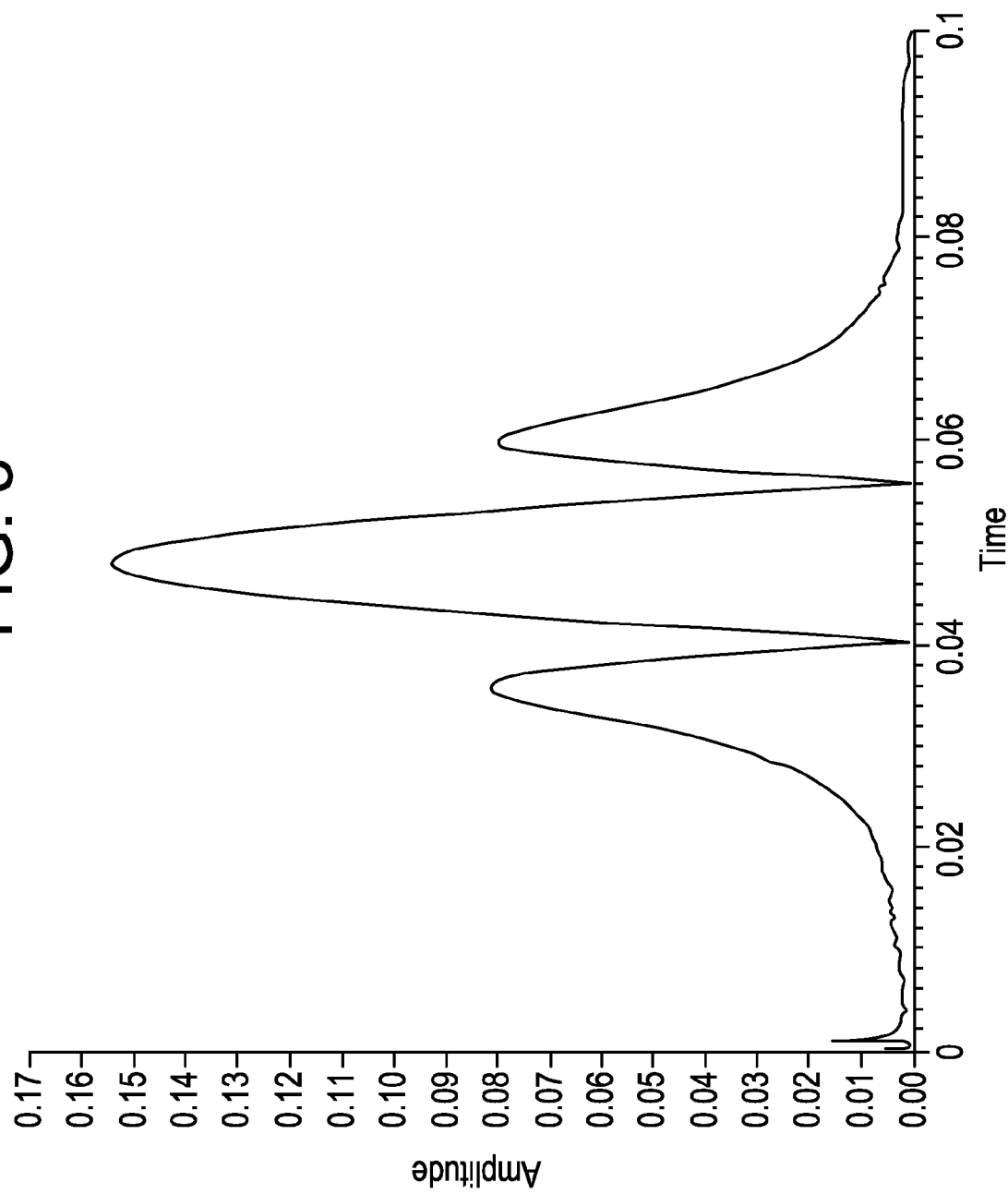
FIG. 3 illustrates an example of an absorbance-based 2f lineshape recorded by an absorbance-based wavelength-modulation spectroscopy apparatus in one embodiment of the invention.

In another aspect, when the absorbance $A(\nu)$ is determined based on the ratio of the monochromatic radiation intensities $I_0(\nu)$ and $I(\nu)$, any intensity modulation of the monochromic radiation as a by-product of wavelength modulation can be cancelled out. In other words, the intensity modulation has no effect on the absorbance $A(\nu)$. This frees absorbance-based wavelength-modulation spectroscopy from contamination and lineshape distortion by other harmonics, which usually can be caused by the concurring intensity modulation. FIG. 3 illustrates an example of an absorbance-based 2f lineshape recorded with a dual phase software lock-in.

In another aspect, the common-mode noise existing in the intensities $I_0(\nu)$ and $I(\nu)$, such as laser noise including laser power decline due to aging, can also be cancelled out. Unlike other common-mode noise cancellation techniques, the absorbance-based wavelength-modulation spectroscopy method of the invention does not require balancing the measurement and reference signal magnitudes.

In another aspect, the absorbance-based wavelength-modulation spectroscopy method of the invention can utilize a phase-sensitive detection technique. Due to the common-mode noise cancellation and phase-sensitive detection, the absorbance-based wavelength-modulation spectroscopy method of the invention can be one of the most sensitive spectroscopy techniques.

In another aspect, the absorbance-based wavelength-modulation spectroscopy method can be insensitive to a drift in the photosensitivity of detectors that are used to measure light intensity, or in the gain of subsequent preamplifiers, since any DC component of the absorbance $A(v)$ can be eliminated upon demodulation, as can be seen from the equation (4). A drift in the photosensitivity of detectors or in the gain of preamplifiers, both of which can be caused by a change in ambient temperature, only adds a DC offset to $A(v)$ that is not wavelength-specific, and thus can be automatically nullified by demodulation.

In another aspect, the harmonic spectrum can be directly derived from Beer-Lambert law, involving no approximation. At a given electromagnetic frequency, the harmonic spectrum can be determined by the sample and the absorption path length only. Variations of the monochromatic radiation source, photodetectors, and associated electronics have little effect on the harmonic spectrum, thus significantly improving the accuracy of the spectroscopy apparatus according to the invention.

Figure 4:
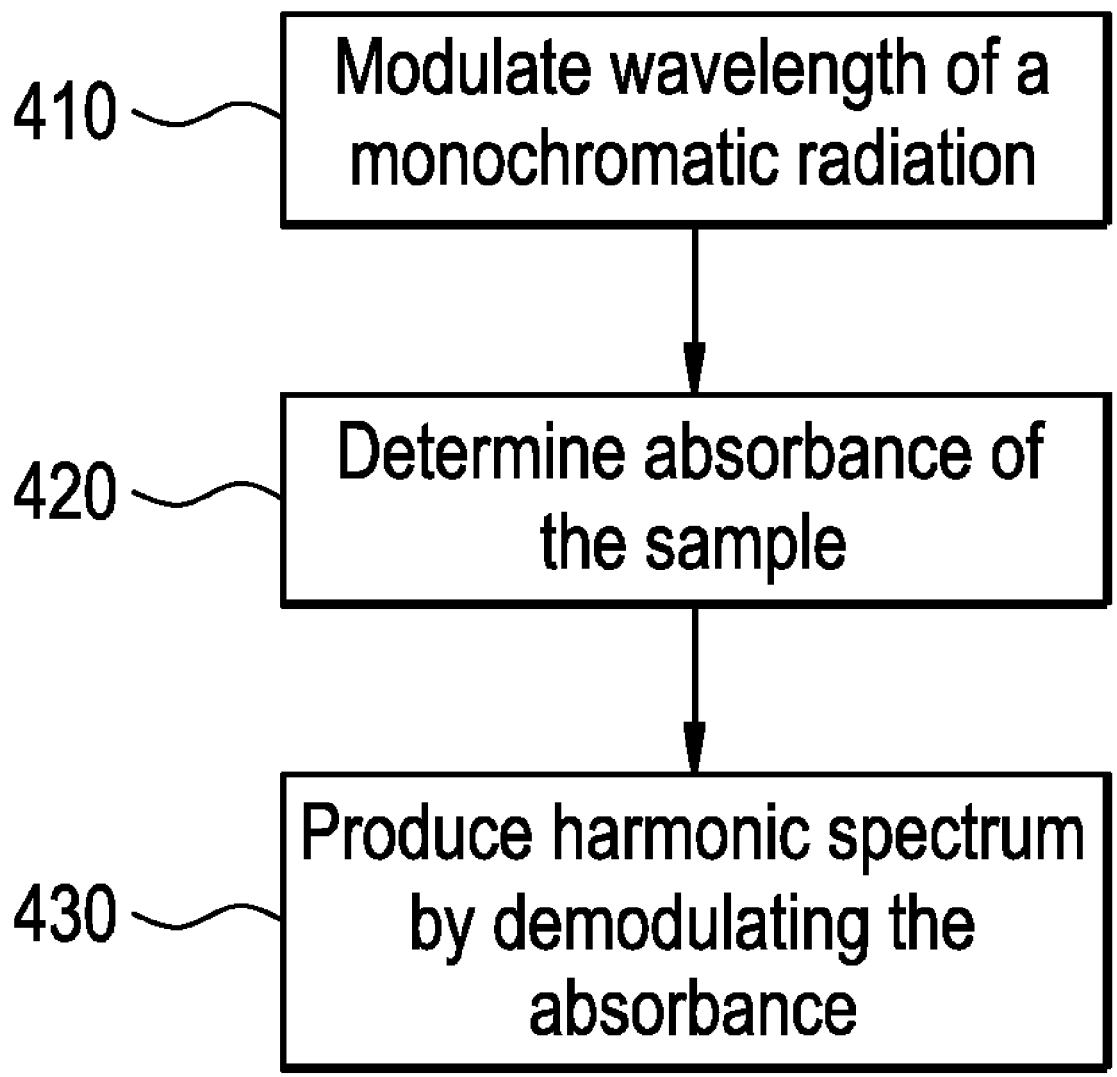
FIG. 4 illustrates a flowchart of the method of absorbance-based wavelength-modulation spectroscopy in one embodiment of the invention.

A flowchart illustrating one embodiment of an absorbance-based wavelength-modulated spectroscopy method according to the invention is illustrated in FIG. 4.

At step 410, a monochromatic radiation emitted by the monochromatic radiation emitting device 115, can be wavelength-modulated at a modulation frequency, in accordance with equation (3).

At step 420, the absorbance $A(v)$ of a sample can be determined. In one embodiment, the absorbance of the sample is determined as the natural logarithm of the ratio of the intensity of monochromatic radiation $I_0(v)$ entering the sample to the intensity of monochromatic radiation $I(v)$ exiting the sample, at the electromagnetic frequency $v$, according to the equation (1).

Direct, real-time measurement of the intensity $I_0(v)$ of the monochromatic radiation entering a sample is recognized to be difficult. However, scaling the intensity $I_0(v)$ only adds a DC offset to the absorbance $A(v)$ and thus does not alter the resulting spectrum. Hence, other measurements can be used to substitute for the intensity $I_0(v)$ of the monochromatic radiation entering a sample. For example, when the monochromatic radiation is provided by a laser diode, the intensity of back emission of the diode, or the diode laser drive waveform corrected to reflect diode laser nonlinearity, is proportional to the actual $I_0(v)$, and thus can be used to substitute for $I_0(v)$. More generally, when the monochromatic radiation is provided by a laser emitting device, the intensity of a light split from the laser beam incident on the sample is proportional to the actual intensity $I_0(v)$ entering the sample, and thus can be used to substitute for $I_0(v)$. A substitution by any of these variables representative of the intensity $I_0(v)$ does not compromise the validity and accuracy of the resulting harmonic spectrum. In another embodiment, the intensity $I_0(v)$ can be measured in advance with no absorbent in the beam path.

In one embodiment, substituting in step 420 a variable representative of the intensity $I_0(v)$ of the monochromatic radiation entering the sample for the intensity $I_0(v)$ itself would produce a variable representative of the absorbance. In another embodiment, substituting in step 420 a variable representative of the intensity $I_0(v)$ of the monochromatic radiation entering the sample for the intensity $I_0(v)$ itself would produce the absorbance with a DC offset.

At step 430, the absorbance of the sample can be demodulated at a harmonic of the modulation frequency to produce a harmonic spectrum of the analyte in the sample, as illustrated by the equation (4). In one embodiment of the invention, demodulation can be performed at the second harmonic of the modulation frequency. A skilled artisan would appreciate the fact that performing demodulation at other harmonics is within the scope and the spirit of the invention.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A spectroscopy method comprising the steps of:
   modulating the wavelength of a monochromatic radiation at a modulation amplitude and a modulation frequency;
   determining a first variable representative of an absorbance of an analyte in a sample; and
   demodulating by phase-sensitive detection said first variable at a harmonic of said modulation frequency to produce a harmonic spectrum of said analyte.

2. The method of claim 1, wherein said monochromatic radiation is provided by a laser.

3. The method of claim 1, wherein said first variable is provided by an absorbance of said analyte in said sample and is based on the intensity of said monochromatic radiation exiting said sample and the intensity of said monochromatic radiation entering said sample.

4. The method of claim 1, wherein said first variable is provided by an absorbance of said analyte in said sample with a DC offset and is based on the intensity of said monochromatic radiation exiting said sample and a second variable that is proportional to the intensity of said monochromatic radiation entering said sample.

5. The method of claim 4, wherein said second variable is determined simultaneously with said intensity of said monochromatic radiation exiting said sample.

6. The method of claim 4, wherein said second variable is determined before said intensity of said monochromatic radiation exiting said sample is determined.

7. The method of claim 1, wherein said harmonic is a second harmonic of said modulation frequency.

8. The method of claim 1, wherein a magnitude of said harmonic spectrum is linearly related to a concentration of said analyte in said sample.

9. A spectroscopy apparatus comprising:
   a laser diode integrated with a first photodetector, said first photodetector configured to detect an intensity of a backward emission from said laser diode and act as a reference detector;
   a second photodetector configured to detect an intensity of laser radiation exiting a sample; and electronic circuitry coupled to said laser diode and said first and second photodetectors, said electronic circuitry configured to acquire and process spectra of said sample.

10. The spectroscopy apparatus of claim 9, wherein said laser diode is further integrated with a thermoelectric cooler and a temperature sensor.

11. The spectroscopy apparatus of claim 9, wherein said apparatus is configured to perform at least one of:
   direct absorption spectroscopy measurement and harmonic spectroscopy measurement.

* * * * *